United States Patent
Sacktor et al.

(10) Patent No.: US 11,446,264 B2
(45) Date of Patent: Sep. 20, 2022

(54) MEMORY MANIPULATION VIA MODIFICATION OF PROTEIN KINASE C ZETA ACTIVITY

(71) Applicants: THE RESEARCH FOUNDATION FOR THE STATE UNIVERSITY OF NEW YORK, Albany, NY (US); UNIVERSITY OF SOUTH FLORIDA, Tampa, FL (US)

(72) Inventors: Todd Sacktor, Brooklyn, NY (US); Mildred Acevedo-Duncan, Plant City, FL (US)

(73) Assignees: THE RESEARCH FOUNDATION FOR THE STATE UNIVERISTY OF NEW YORK, Albany, NY (US); UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/755,423

(22) PCT Filed: Oct. 15, 2018

(86) PCT No.: PCT/US2018/055830
§ 371 (c)(1),
(2) Date: Apr. 10, 2020

(87) PCT Pub. No.: WO2019/075453
PCT Pub. Date: Apr. 18, 2019

(65) Prior Publication Data
US 2020/0261384 A1    Aug. 20, 2020

Related U.S. Application Data

(60) Provisional application No. 62/572,188, filed on Oct. 13, 2017.

(51) Int. Cl.
| | | |
|---|---|---|
| *A61K 31/185* | (2006.01) | |
| *A61P 25/00* | (2006.01) | |
| *A61K 9/16* | (2006.01) | |
| *A61P 25/30* | (2006.01) | |

(52) U.S. Cl.
CPC .......... *A61K 31/185* (2013.01); *A61P 25/00* (2018.01); *A61K 9/1605* (2013.01); *A61P 25/30* (2018.01)

(58) Field of Classification Search
CPC ......... A61K 31/185; A61P 25/00; A61P 25/30
See application file for complete search history.

(56) References Cited

U.S. PATENT DOCUMENTS

| | | |
|---|---|---|
| 7,605,119 B2 | 10/2009 | Sacktor |
| 2009/0318462 A1 | 12/2009 | Antonetti et al. |
| 2015/0366883 A1 | 12/2015 | Acevedo-Duncan et al. |
| 2017/0348336 A1 | 12/2017 | Acevedo-Duncan |
| 2018/0008564 A1* | 1/2018 | Acevedo-Duncan ............ G01N 33/5011 |
| 2020/0078323 A1* | 3/2020 | Acevedo-Duncan ............ A61K 9/0031 |

FOREIGN PATENT DOCUMENTS

| | | | | |
|---|---|---|---|---|
| WO | WO-2004011560 A2 * | 2/2004 | ............ | C09D 11/38 |
| WO | WO-2005058807 A1 * | 6/2005 | ........... | C07D 251/20 |
| WO | 2009026083 A1 | 2/2009 | | |

OTHER PUBLICATIONS

Frankland et al. Nature, Jul. 7, 2016, vol. 535, pp. 41-42 (Year: 2016).*
International Search Report and Written Opinion of the International Searching Authority for International Application No. PCT/US2018/055830 dated Dec. 6, 2019.
Ratnayake, W.S., et al., "Oncogenic PKC-ι activates Vimentin during epithelial-mesenchymal transition in melanoma; a study based on PKC-ι and PKC-ζ specific inhibitors", Cell Adhesion & Migration, vol. 12, No. 5, pp. 447-463 (2018).
Carey, B., "Brain Researchers Open Door to Editing Memory", printed Apr. 6, 2009, <URL:http://www.nytimes.com/2009/04/06/health/research/06brain.html?>.
Chen, C., et al., "Epigenetic modification of PKMι rescues aging-related cognitive impairment", Scientific Reports |6:22096 | DOI: 10.1038/srep22096, pp. 1-17(2016).
Gao, P.P., et al., "Layer-Specific Molecular Dynamics of PKMζ in Sensorimotor Cortex During Acquisition and Storage of Procedural Memory", preprint first posted online Sep. 25, 2017; doi: http://dx.doi.org/10.1101/193508.

(Continued)

*Primary Examiner* — James D. Anderson
(74) *Attorney, Agent, or Firm* — Heslin Rothenberg Farley & Mesiti P.C.

(57) ABSTRACT

Provided is a method of inhibiting protein kinase C zeta/protein kinase M zeta, including contacting a sample containing an isoform of protein kinase C zeta with a compound of formula: referred to as 1-naphthol-3,6,8-trisulphonic acid, or a pharmaceutically acceptable salt thereof. In some embodiments, contacting the sample with the compound does not inhibit protein kinase C iota/lambda. In a specific example, the sample includes neural tissue, the isoform of protein kinase C zeta is protein kinase M zeta, and inhibiting includes reducing kinase activity and further includes diminishing long-term potentiation. In some embodiment, the method includes inhibiting glucose transport. Also provided is a method of affecting memory, including administering the compounds to a mammalian organism.

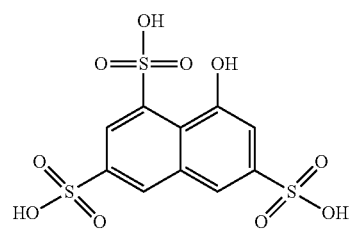

9 Claims, 4 Drawing Sheets

(56) References Cited

OTHER PUBLICATIONS

Hara, Y., et al., "Synaptic distributions of GluA2 and PKM ζ in the monkey dentate gyrus and their relationships with aging and memory", J Neurosci., vol. 32, No. 21, pp. 7336-7344 (2012).
Morris, R.G.M., "Forget me not An enzyme called PKM zeta may have a role in long-term memory after all", eLife; 5:e16597. DOI: 10/7554/eLife.16597, pp. 1-2 (2016).
Pastalkova, E., et al., "Storage of Spatial Information by the Maintenance Mechanism of LTP", Science, vol. 313, pp. 1141-1144 (2006).
Tsokas, P., et al., "Compensation for PKMζ in long-term potentiation and spatial long-term memory in mutant mice", eLife; 5:e14846. DOI: 10.7554/eLife.14846 (2016).

* cited by examiner

MEMORY MANIPULATION VIA MODIFICATION OF PROTEIN KINASE C ZETA ACTIVITY

CROSS REFERENCE TO RELATED APPLICATIONS

This application is a national stage filing under 35 U.S.C. § 371 of International Application No. PCT/US2018/055830, filed on Oct. 15, 2018, published as WO 2019075453 on Apr. 18, 2019, and claims priority to U.S. Provisional Patent Application 62/572,188, filed Oct. 13, 2017. The entire disclosures of each of the said applications are incorporated by reference in their entireties herein.

GOVERNMENT RIGHTS STATEMENT

This invention was made with Government support under grant number MH057068 awarded by the National Institutes of Health. The Government has certain rights in the invention.

FIELD OF THE INVENTION

This disclosure relates to methods of manipulating memory and cellular process related to memory formation and recall. More particularly, disclosed herein are compositions and methods for modifying activity of molecular mechanisms related to memory and associated neural processes and their applicability for modifying mental states and behavioral tendencies.

BACKGROUND OF THE INVENTION

During learning, neurons produce an enzyme called PKC zeta/PKM zeta which is responsible for maintaining newly strengthened connections between neurons and for memory. PKC zeta includes a catalytic domain at its C-terminus and a regulatory domain at its N-terminus, joined by a hinge region. The regulatory region binds to the catalytic domain and inhibits its kinase activity. PKM zeta is a truncation of PKC zeta expressed in neurons which is constitutively active because it lacks the autoinhibitory N-terminus. Inhibitors of PKC zeta/PKM zeta activity or expression disrupt long-term memories and modifications of synaptic activity attendant to the strengthening of synaptic communication that follows application high-frequency stimulation such as long-term potentiation. However, the availability of compounds that selectively affect activity of PKC zeta/PKM zeta, without affecting other PKC isoforms, such as PKC alpha, PKC beta, or PKC iota/lambda, is lacking. Furthermore, compounds that affect PKC zeta/PKM zeta but are also capable of penetrating cell membranes or the blood-brain barrier are not known.

Numerous memory and mood disorders, and other disorders such as neuropathic pain, are believed to be due to pathological processes related to memory, including processes involving activity of PKC zeta/PKM zeta. Compounds that could cross the blood-brain barrier and enter cell membranes to contact intracellular PKC zeta/PKM zeta, within neurons, are therefore desirable, such as for use as treatments for various mood- and memory-related disorders or neuropathic pain. The present disclosure is directed to overcoming these and other deficiencies in the art.

SUMMARY OF THE INVENTION

In one aspect, this disclosure relates to a method of inhibiting protein kinase C zeta, including contacting a sample containing an isoform of protein kinase C zeta with a compound of formula:

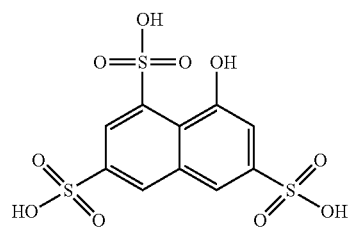

or a pharmaceutically acceptable salt thereof. In some embodiments, the isoform of protein kinase C zeta is protein kinase M zeta. In another embodiment, inhibiting includes reducing kinase activity. In a further embodiment, the sample includes a tissue sample. For example, the sample may include neural tissue. In yet another embodiment, the method includes affecting synaptic activity. In some examples, affecting synaptic activity includes diminishing long-term potentiation. In some embodiments, contacting the sample with the compound does not include inhibiting protein kinase C iota/lambda. In a specific example, the sample includes neural tissue, the isoform of protein kinase C zeta is protein kinase M zeta, and inhibiting includes reducing kinase activity and further includes diminishing synaptic long-term potentiation. In some embodiments, the method includes inhibiting glucose transport.

In another aspect, the present disclosure relates to a method of affecting memory, including administering to a mammalian organism a compound of formula:

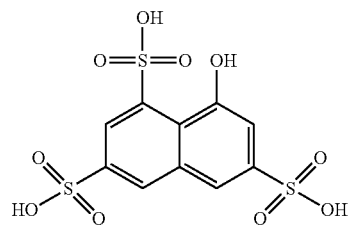

or a pharmaceutically acceptable salt thereof. In some embodiments, administering includes administering orally, intramuscularly, subcutaneously, intraperitoneally, intrathecally, or intracranially. In other embodiments, the organism includes a rodent or a primate. In still other embodiments, affecting comprises interfering with long-term memory retrieval. In some examples, long-term memory retrieval includes spatial memory, emotional memory, addiction, neuropathic pain, visual recognition memory, declarative memory, or episodic memory. In yet other embodiments, the compound contacts neural tissue. In some examples, the neural tissue is cortical tissue, septohippocampal tissue, amygdalar tissue, striatal tissue, spinal cord tissue, or cerebellar tissue. Other embodiments include administering the compound admixed with a pharmaceutically acceptable excipient. In yet other embodiments, a complex is formed between the compound and an isoform of protein kinase C zeta. In a specific example, affecting memory includes medical treatment and the organism is a human in need of said medical treatment, and the method includes administering the compound or pharmaceutically acceptable salt thereof admixed with a pharmaceutically acceptable excipient.

BRIEF DESCRIPTION OF THE DRAWINGS

These and other features, aspects, and advantages of the present disclosure will become better understood when the following detailed description is read with reference to the accompanying drawings, wherein.

DETAILED DESCRIPTION OF THE INVENTION

Figure 1:
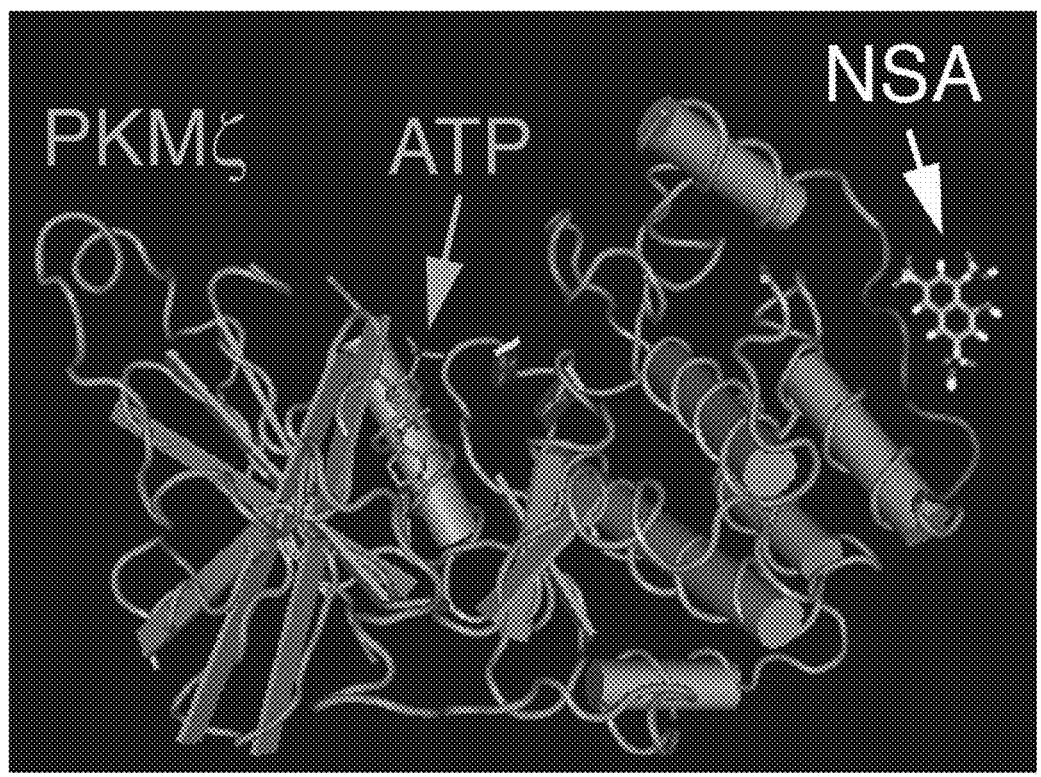
FIG. 1 shows an illustration of 1-naphthol-3,6,8-trisulphonic acid (NSA) binding to a site present in protein kinase C zeta/protein kinase M zeta (PKC zeta/PKM zeta) that is absent from other kinases.

Aspects of subject matter disclosed herein and certain features, advantages, and details thereof, are explained more fully below with reference to non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating some embodiments, are given by way of illustration only, and are not by way of limitation. Various substitutions, modifications, additions and/or arrangements within the spirit and/or scope of the underlying inventive concepts will be apparent to those skilled in the art from this disclosure.

This disclosure relates to a method of inhibiting protein kinase C zeta, including contacting a sample containing an isoform of protein kinase C zeta with a compound of formula:

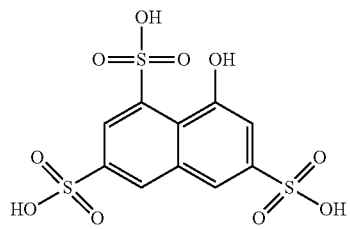

or a pharmaceutically acceptable salt thereof. In some embodiments, the isoform of protein kinase C zeta is protein kinase M zeta. In another embodiment, inhibiting includes reducing kinase activity. In a further embodiment, the sample includes a tissue sample. For example, the sample may include neural tissue. In yet another embodiment, the method includes affecting synaptic activity. In some examples, affecting synaptic activity includes diminishing long-term potentiation. In some embodiments, contacting the sample with the compound does not include inhibiting protein kinase C iota/lambda. In a specific example, the sample includes neural tissue, the isoform of protein kinase C zeta is protein kinase M zeta, and inhibiting includes reducing kinase activity and further includes diminishing long-term potentiation. In some embodiment, the method includes inhibiting glucose transport.

In another aspect, the present disclosure relates to a method of affecting memory, including administering to a mammalian organism a compound of formula:

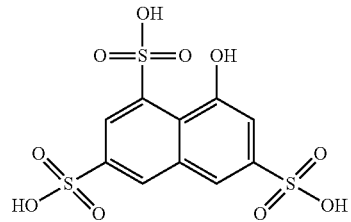

or a pharmaceutically acceptable salt thereof. In some embodiments, administering includes administering orally, intramuscularly, subcutaneously, intraperitoneally, intrathecally, or intracranially. In other embodiments, the organism includes a rodent or a primate. In still other embodiments, affecting comprises interfering with long-term memory retrieval. In some examples, long-term memory retrieval includes spatial memory, emotional memory, addiction, neuropathic pain, visual recognition memory, declarative memory, or episodic memory. In yet other embodiments, the compound contacts neural tissue. In some examples, the neural tissue is cortical tissue, septohippocampal tissue, amygdalar tissue, striatal tissue, spinal cord tissue, or cerebellar tissue. In other embodiments, the compound was admixed with a pharmaceutically acceptable excipient. In yet other embodiments, a complex is formed between the compound and an isoform of protein kinase C zeta. In a specific example, affecting memory includes medical treatment, the compound or pharmaceutically acceptable salt thereof was admixed with a pharmaceutically acceptable excipient, and the organism is a human in need of said medical treatment.

As disclosed herein, administration of NSA, represented by formula:

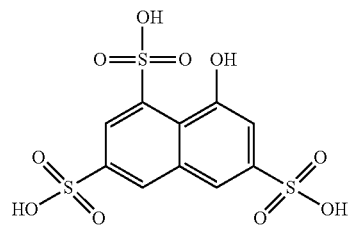 [SMILES: O=S(=O)(O)c1cc(O)c2c(S(=O)(=O)O)cc(S(=O)(=O)O)cc2c1]

to a sample can inhibit kinase activity of PKC zeta/PKM zeta. NSA may form a complex with PKC zeta/PKM zeta by binding to a site therein and thereby preventing PKC zeta/PKM zeta from binding with molecular targets or catalyzing enzymatic reactions such as phosphorylation. PKC zeta/PKM zeta is known to have various functions. One function, including activity in neurons, relates to the ability of neurons to undergo alterations in responsiveness to synaptic transmission.

For example, in response to excitatory stimulation, neurons may exhibit a phenomenon known as long-term potentiation (LTP), in which responsiveness of a neuron to a given amount of synaptic input may increase following receipt of high-frequency stimulation said synaptic input. LTP, as is understood by those with skill in the field to which this disclosure pertains, can be established across a chemical synapse by applying high-frequency (e.g., 100 Hz) stimulation to the pre-synaptic afferent and measuring the response of the post-synaptic neuron (e.g., excitatory post-synaptic potentials) in response to subsequent pre-synaptic stimulation. Such tetanizing stimulation may lead to increased post-synaptic activity in response to a given amount of pre-synaptic stimulation (e.g., an increase in the magnitude of excitatory postsynaptic potentials in response to a given amount of stimulation of the pre-synaptic input after application of tetanizing stimulation compared to before). PKC zeta/PKM zeta is known to play a significant role in neurons' ability to maintain LTP once it is formed. For example, applying compounds that inhibit PKC zeta/PKM zeta kinase activity after LTP formation leads to a reduction of LTP.

As disclosed herein, NSA binds to a region of PKC zeta/PKM zeta enzyme, a region not present in other forms of PKC such as PKC alpha, beta, or iota/lambda. See FIG. 1. Furthermore, NSA inhibits kinase activity of PKC zeta/PKM zeta but not kinase activity of other PKC enzymes such as PKC iota/lambda. Whereas PKC zeta/PKM zeta affects LTP, in particular maintenance of LTP after its formation, the ability of NSA to bind PKC zeta/PKM zeta and affect its kinase activity, differentially from binding to or influencing the activity of other enzymes including other isoforms of PKC, NSA may particularly influence functions for which PKC zeta/PKM zeta has a mechanistic function that is distinct or different from those of other kinases. For example, whatever functions PKC alpha, beta, or lambda/iota may have, such as in LTP or learning and memory or otherwise, NSA may be used to specifically interfere with the functions of PKC zeta/PKM zeta without impairing or otherwise influencing functions of PKC alpha, beta, or lambda/iota.

As disclosed herein, NSA may be applied to a sample. A sample may be a subject, such as a mammalian organism. For example, NSA may be applied to a primate or rodent, or other mammal. For example, NSA could be applied to a human or a chimpanzee. NSA could also be applied to a rat, mouse, gerbil, guinea pig, hamster, or vole. Also as disclosed herein, NSA may be applied to other mammalian species, such as of sheep, goat, horse, dog, cat, or pig. As those with skill in the pertinent field would apprehend, known similarities between the structure and function of PKC zeta/PKM zeta between these species indicate correspondingly similar effects of PKC zeta/PKM zeta and of NSA thereupon. For example, NSA may be used to inhibit activity of PKC zeta/PKM zeta in the foregoing species or other mammalian species. Moreover, NSA may be used to inhibit activity of PKC zeta/PKM zeta, without inhibiting activity of, or at doses that do not inhibit activity of, other enzymes, such as PKC alpha, beta, or lambda/iota, in the foregoing species or other mammalian species.

A sample may include tissue from any of the foregoing or other species. For example, NSA may be applied to neural tissue taken from such a species. For example, sections of neural tissue may be taken from a subject, such as a rodent subject such as a mouse or rat or other rodent (or other mammalian species) and subjected to stimulation known to cause modifications in cells' responsiveness to subsequent stimulation or other input, and NSA may be applied to such sample to determine whether NSA affects such activity or responsiveness. For example, an effect of NSA on the formation or maintenance of LTP may be used to determine whether PKC zeta/PKM zeta is important for such a phenomenon. In an example, application of NSA to a sample of neural tissue that diminishes LTP or other index of synaptic plasticity may demonstrate that PKC zeta/PKM zeta is important for maintenance of LTP. A sample of neural tissue may include tissue from the cerebral cortex, hippocampus, septum (or septohippocampal system), amygdala, striatum, cerebellum, spinal cord, or other regions of the central nervous system.

In other examples, a sample may include other types of cells taken from any of the foregoing species, and NSA may be applied to such sample to determine whether PKC zeta/PKM zeta is involved in regulating or influencing a given function or cellular or molecular phenomenon in such sample. As but one non-limiting example, various stimuli, including contacting a cell with insulin, is known to influence transport of glucose across the membrane of such cell. PKC zeta in particular is known to be involved in stimulation of glucose transport, caused by insulin or by glucose itself (e.g., glucose-mediated glucose transport in hyperglycemia). In some examples, adipose cells or muscle cells exhibit insulin-stimulated glucose transport, which involves PKC zeta/PKM zeta. As disclosed herein, NSA may be applied to samples of tissue, such as samples of adipose tissue or muscle tissue, or other tissue in which mechanisms of mediating glucose transport are of interest, to determine or examine a role of PKC zeta/PKM zeta in modifying such activity. For example, NSA may be applied to a sample of muscle, adipose, or other tissue, or to an organism, including any of the organisms identified above, to inhibit or blunt glucose transport.

NSA may bind to and inhibit kinase activity of different forms of PKC zeta. For example, NSA binds to a region of PKC zeta that is also present in a form of the kinase enzyme expressed in neurons referred to as PKM zeta. As disclosed herein, NSA may be used to interfere with the activity or binding of both forms of the enzyme. Unless otherwise specified, effects of NSA on PKC zeta or activity thereof, or on PKM zeta or activity thereof, are intended to indicate such activity on both of these forms of the enzyme. PKM zeta is referred to herein as an isoform of PKC zeta in that both share a catalytic domain.

Learning and memory as used herein may refer to numerous molecular, cellular, neural, mental, emotional, or behavioral phenomena. In some instances, memory refers to an ability to recall particular events, emotions, facts, sensations, etc., referred to as explicit or declarative memory. In some examples, memory may involve memory for spatial relationships between places or events, and may be referred to as spatial memory. In still other examples, memory may involve memory of associations between stimuli and affective states, such as fear, hungry, affiliation, disgust (e.g., conditioned taste aversion), etc. In other examples, memory may involve a combination of any of the foregoing functions.

In some examples, memory may be related to pathological processes, such as depression or depression-related phenotypes, such as are modelled in animal models of anxiety and depression such as learned helplessness, immobilization, chronic stress administration, or forced swim paradigms. In such examples, an animal may be exposed to noxious or unpleasant stimuli and subsequent modification of behavioral responsiveness to other input that had been temporally associated with such stimuli, or of active behavioral responses to repetition of such noxious or unpleasant stimuli, measured. In such models, administration of therapeutically effective treatments for mood disorders are capable of preventing, reversing, or reducing the effects of such stimulus exposure. Disruption of PKC zeta/PKM zeta activity is known to block or reverse behavioral sequelae of such stimuli. For example, exposing rodents to chronic stress is known to have anxiogenic effects in several behavioral paradigms such as the open field test and the elevated plus maze, and to induce a depression-like phenotype in animal models such as causing increased immobility in the forced swim test. Exposure to chronic stress also increases expression of PKM zeta in the brain, and inhibition of PKC zeta/PKM zeta activity reduces these behavioral effects of chronic stress, indicating that it functions like an anxiolytic compound or antidepressant compound. In accordance with the present disclosure, NSA may be administered to subjects, such as animals or humans, subjected to various noxious or unpleasant stimuli to reverse the affective and behavioral consequence of such stimulus exposure.

As further disclosed herein, mood disorders believed to result from persistent memory functions related to neural processes underlying negative affect or recollection of or perseverative cognition of painful, frightening, or unpleasant stimuli may result from activity of PKC zeta/PKM zeta reinforcing activity of neural systems responsible for such persistent memory functions. As disclosed herein, NSA may be administered as a treatment for such mood disorders. For example, as disclosed herein, NSA may be administered as a treatment for post-traumatic stress disorder, depression, anxiety, or phobia. In some examples, such disorders are or may have been caused by prior experiences, and therefore reducing activity of PKC zeta/PKM zeta may function to reduce or eliminate pathological processes caused by such experiences and causally related to such mood disorders or symptoms thereof. For example, a person may have been exposed to traumatic experiences and developed an affective disorder requiring treatment, such as a treatment to alleviate or reduce memory-related mechanisms triggered by such experiences resulting in the affective or mood disorder. NSA may be administered to such individuals to effect such treatment.

In some examples, NSA may be administered as an adjunctive therapy along with treatment with a different therapy such as a pharmacological therapy, shock therapy, or other treatment for affective disorders. In some examples, NSA may be administered to individuals undergoing cognitive, behavioral, or psychoanalytical therapy, whether in addition to other pharmacological treatment or not, where such treatment is performed for the purpose of extinction of memories with pathological influence.

In other examples, exposure to positively motivating stimuli may affect subsequent responsiveness to such stimuli or other input spatially or temporally associated therewith. For example, repeated exposure to drugs of abuse such as cocaine, opiates, amphetamines, marijuana or cannabinoids, nicotine, or other stimulants, narcotics, anesthetics, anxiolytics, or to alcohol, or other addictive substances may alter neural function resulting in pathological behaviors directed towards continued consumption of such stimuli. Memory-related mechanisms are known to be engaged in the behavioral and affective changes that follow from exposure to drugs of abuse. In animal models, inhibition of PKC zeta/PKM zeta is known to impair behavioral sequelae of exposure to drugs of abuse, in models considered animal models of addiction. In such models, treatments that prevent, reduce, or reverse the affective or behavioral effects of exposure to drugs of abuse may be effective as treatments for drug addiction or alcohol. For example, conditioned placed preference models, self-administration models, and locomotor sensitization models are examples of animal models of drug addiction. For example, exposure to morphine increase PKM zeta expression in brain regions known to be important in development of drug addiction, and inhibiting PKC zeta/PKM zeta activity prevents behavioral modification caused by exposure to morphine such as development of a conditioned place preference. Inhibiting PKC zeta/PKM zeta activity in such models by administering NSA, as disclosed herein, may prevent, reverse, or reduce the behavioral or affective sequelae of drug or alcohol exposure in such models. As further disclosed herein, NSA administration to humans may be used for prevention of craving or drug seeking behavior, or otherwise as a treatment for drug addiction or alcoholism. For example, NSA may be administered to drug-addicted individuals, in need of a treatment to prevent drug-seeking, drug-taking, drug-craving, or relapse from abstinence. NSA may be administered on its own, or may be administered as an adjunct to other therapy for addiction. In some examples, NSA may be administered to individuals undergoing cognitive, behavioral, or psychoanalytical therapy, whether in addition to other pharmacological treatment or not, where such treatment is performed for the purpose of treating drug addiction or alcoholism.

In other examples, stimuli or experience may affect neural function leading to aberrant, persistent sensation of pain, or hypersensitivity to previously mildly painful stimuli, or an ability of previously non-painful stimuli to cause pain. Referred to generally as neuropathic pain, such functions are known to involve activity of PKC zeta/PKM zeta for their maintenance. Examples may include phantom limb pain, nerve damage, nerve trauma, neuropathy (e.g., diabetic neuropathy), cancer pain, or other known or undiagnosed causes of paid related to aberrant neural function. For example, damage to somatosensory peripheral nerves can modify central nervous system processes such that pain may be perceived in the absence of application of pain-inducing stimuli, and/or perceptual or behavioral responses to noxious or painful stimuli may become enhanced or exaggerated (e.g., previously mildly noxious or painful stimuli may come to elicit a higher degree of pain). Neural mechanisms related to memory, such as the formation or maintenance of LTP, are known to be involved in neuropathic pain. Activity of PKC zeta/PKM zeta in the nervous system is known to be involved in regulation of neural processing attendant to development of neuropathic pain in response to different stimuli and experiences, and inhibition of PKC zeta/PKM zeta diminishes indices of neuropathic pain in animal models related to such phenomena. For example, in animal models, such as the mechanical allodynia test, inhibition of PKC zeta/PKM zeta activity increases the threshold for tactile stimuli to induce a withdrawal response following peripheral nerve injury, indicating inhibition of neuropathic pain processes. As disclosed herein, NSA may be administered as a treatment for neuropathic pain, such as to reduce human patients' persistent sensation or perception of pain caused by or consequent to pathophysiological processes or physiological damage or disruption to normal physiological processes related to perception or sensation of pain.

Formulations for administration to a subject include, without limitation, those suitable for oral, parenteral (including subcutaneous, intradermal, intramuscular, intravenous and intraarticular), rectal and topical (including dermal, buccal, sublingual and intraocular) administration, or any and all other routes or methods of administration as further disclosed herein. The most suitable route may depend upon the condition and disorder of a recipient or intended purpose of the administration. A formulation may conveniently be presented in unit dosage form and may be prepared by any of the methods well known in the art of pharmacy. Methods may include a step of bringing into association NSA or a pharmaceutically acceptable salt thereof ("active ingredient") with a carrier which constitutes one or more accessory ingredients. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. NSA may also be presented as a bolus, electuary or paste. For oral or other administration, NSA may be suspended in a solution, or dissolved in a solvent, such as alcohol, DMSO, water, saline, or other solvent, which may be further diluted or dissolved in another solution or solvent, and may or may contain a carrier or other excipient in some examples.

In certain embodiments, NSA may be incorporated with excipients and used in the form of ingestible tablets, buccal tablets, troches, capsules, elixirs, suspensions, syrups, wafers, and the like. Tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

A tablet may be made by compression or molding, optionally with one or more accessory ingredients. Compressed tablets may be prepared by compressing in a suitable machine an active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. Tablets may optionally be coated or scored and may be formulated so as to provide sustained, delayed or controlled release of an active ingredient therein.

Formulations for parenteral or other administration include aqueous and non-aqueous sterile injection solutions which may contain anti-oxidants, buffers, bacteriostats and solutes which render a formulation isotonic with the blood of the intended recipient. Formulations for parenteral or other administration also may include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of NSA to polymer and the nature of the particular polymer employed, the rate of NSA release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

An NSA formulation may include different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

NSA may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of Burger's Medicinal Chemistry And Drug Discovery, 5 th Edition, Vol 1: Principles and Practice.

As used herein, the term "effective amount" means an amount of an NSA pharmaceutical agent that may elicit a biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of NSA, as well as salts, solvates, and physiological functional derivatives thereof, may be administered as the raw chemical. Additionally, the active ingredient may be presented as a pharmaceutical composition.

Pharmaceutical compositions of the present invention include an effective amount of NSA and optionally one or more additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains NSA and optionally one or more additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

Further in accordance with the present invention, the composition of the present invention suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, NSA may be combined with a carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of pharmaceutical lipid vehicle compositions that include NSA and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, NSA may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to a subject (e.g., an animal or human patient) can be determined by physical and physiological factors such as body weight, severity of condition, the type of disease being treated, previous or concurrent therapeutic interventions, idiopathy of the patient and on the route of administration, and purpose of treatment. Depending upon the dosage and the route of administration, the number of administrations of a preferred dosage and/or an effective amount may vary according to the response of the subject or purpose of treatment. The practitioner responsible for administration will, in any event, determine the concentration of active ingredient(s) in a composition and appropriate dose(s) for the individual subject.

In certain embodiments, pharmaceutical compositions may include, for example, at least about 0.1% of an active compound. In other embodiments, an active compound may comprise between about 2% to about 75% of the weight of the unit, or between about 25% to about 60%, for example, and any range derivable therein. Naturally, the amount of NSA in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

In other non-limiting examples, a dose may also comprise from about 1 microgram/kg body weight, about 5 microgram/kg body weight, about 10 microgram/kg body weight, about 50 microgram/kg/body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above.

Dosing can be modified or chosen based on factors including purpose of treatment, severity of symptoms, or an individual subject's body mass. A daily dose may be administered once per day, or distributed over 2, 3, 4, 5, 6, 7, 8, or more administrations per day. A daily dose may be between 10 mg and 20 g per day. A daily dose may be less than 10 mg, for example 5 mg or 1 mg per day, or in a range of between 1-5 mg or between 5-10 mg. A daily dose may be between 10 mg and 50 mg, or between 50 mg and 100 mg, or between 100 mg and 150 mg, or between 150 mg and 200 mg, or between 200 mg and 250 mg, or between 250 mg and 300 mg, or between 300 mg and 350 mg or between 350 m and 400 mg or between 400 mg and 450 mg or between 450 mg and 500 mg. A daily dose may be between 500 mg and 600 mg, or between 600 mg and 700 mg, or between 700 mg and 800 mg, or between 900 mg and 1 g, or between 1 g and 1500 mg, or between 1500 mg and 2 g, or between 2 g and 2500 mg, or between 2500 mg and 3 g, or between 3 g and 3500 mg, or between 3500 mg and 4 g, or between 4 g and 4500 mg, or between 4500 mg and 5 g. A daily dose may be between 5 g and 6 g, or between 6 g and 7 g, or between 7 g and 8 g, or between 8 g and 9 g, or between 9 g and 10 g, or between 10 g and 11 g, or between 11 g and 12 g, or between 12 and 13 g, or between 13 g and 14 g, or between 14 g and 15 g, or between 15 g and 16 g, or between 16 g and 17 g, or between 17 g and 18 g, or between 18 g and 19 g, or between 19 g and 20 g. All subranges within and between any of these ranges are also included within the present disclosure.

In some embodiments, NSA may be formulated to be administered via an alimentary route. Alimentary routes include all possible routes of administration in which the composition is in direct contact with the alimentary tract. Specifically, NSA may be administered orally, buccally, rectally, or sublingually. As such, NSA may be formulated with an inert diluent or with an assimilable edible carrier, or may be enclosed in hard- or soft-shell gelatin capsule, or may be compressed into tablets, or may be incorporated directly with the food of the diet.

For oral administration NSA may alternatively be incorporated with one or more excipients in the form of a mouthwash, dentifrice, buccal tablet, oral spray, or sublingual orally-administered formulation. For example, a mouthwash may be prepared incorporating NSA in the required amount in an appropriate solvent, such as a sodium borate solution (Dobell's Solution). Alternatively, NSA may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, NSA may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the NSA may be administered via a parenteral route. As used herein, the term "parenteral" includes routes that bypass the alimentary tract. Specifically, NSA may be administered for example, but not limited to intravenously, intradermally, intramuscularly, intraarterially, intrathecally, subcutaneous, or intraperitoneally.

Solutions of NSA as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form may be sterile and fluid to the extent that easy injectability exists. A carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered if necessary and a liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, general safety and purity standards as required by FDA Office of Biologics standards.

Sterile injectable solutions may be prepared by incorporating NSA in the required amount in the appropriate solvent with various of the other ingredients enumerated above, as required, followed by filtered sterilization. Generally, dispersions may be prepared by incorporating various sterilized active ingredients into a sterile vehicle which contains the basic dispersion medium and the required other ingredients from those enumerated above. In the case of sterile powders for the preparation of sterile injectable solutions, preferred methods of preparation include vacuum-drying and freeze-drying techniques which yield a powder of the active ingredient plus any additional desired ingredient from a previously sterile-filtered solution thereof. A powdered composition may be combined with a liquid carrier such as, e.g., water or a saline solution, with or without a stabilizing agent.

In other embodiments NSA may be formulated for administration via various miscellaneous routes, for example, topical (i.e., transdermal) administration, mucosal administration (intranasal, vaginal, etc.) and/or inhalation.

Pharmaceutical compositions for topical administration may include NSA formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described. Likewise, the delivery of drugs using intranasal microparticle resins and lysophosphatidyl-glycerol compounds are also well-known in the pharmaceutical arts. Likewise, transmucosal drug delivery in the form of a polytetrafluoroetheylene support matrix may be adopted for use in accordance with the present disclosure.

The term aerosol refers to a colloidal system of finely divided solid of liquid particles dispersed in a liquefied or pressurized gas propellant. An aerosol of the present invention for inhalation may consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The following examples are intended to illustrate particular embodiments of the present disclosure, but are by no means intended to limit the scope thereof.

As further described below, a compound was developed that inhibits the activity of PKC zeta/PKM zeta protein. The compound, formula:

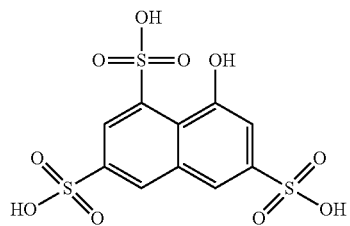 [SMILES: O=S(=O)(O)c1cc(O)c2c(S(=O)(=O)O)cc(S(=O)(=O)O)cc2c1]

or 1-naphthol-3,6,8-trisulphonic acid (NSA), was identified by an in silico screen as capable of binding to PKC zeta/PKM zeta. As illustrated in FIG. 1, NSA binds to a portion of the catalytic domain of PKC zeta/PKM zeta that is not present in any other protein in the NCBI protein database, including other PKC isoforms such as PKC alpha, PKC beta, or PKC iota/lambda. NSA may be administered systemically to cross the blood-brain barrier and access intracellular PKC zeta/PKM zeta.

Figure 2:
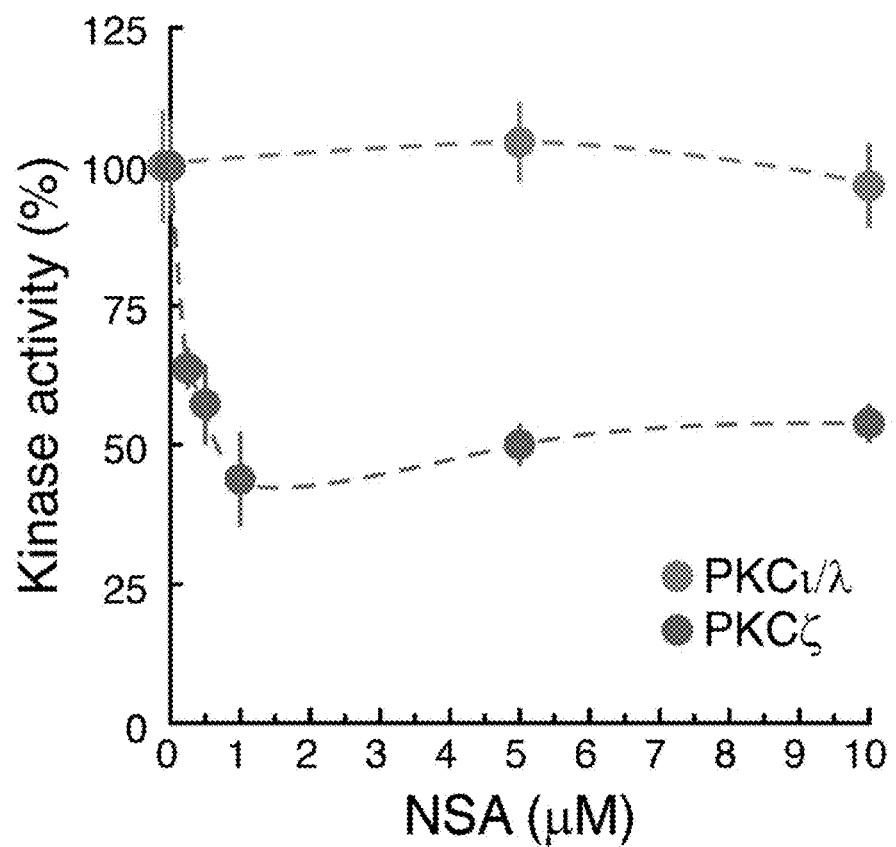
FIG. 2 is a graph showing NSA's ability to inhibit kinase activity of PKC zeta at concentrations at which NSA does not affect kinase activity of PKC iota/lambda.

As shown in FIG. 2 (mean±SEM, ns=3), NSA acts with an $IC_{50}$ of approximately 100 to 200 nM as a negative modulator of PKC zeta/PKM zeta activity, decreasing PKC zeta/PKM zeta activity by approximately 50%, without effect on PKC iota/lambda at doses up to 10 μM. In separate experiments, PKC zeta and PKM zeta were recombinantly expressed and purified. PKC iota/lambda was purchased from ProQinase GmbH (Freiburg, Germany). The reaction mixture (50 ml final volume) contained: 50 mM Tris-HCl (pH 7.4), 10 mM $MgCl_2$, 1 mM DTT, 25 mM e-peptide substrate (ERMRPRKRQGSVRRRV, AnaSpec, Freemont, Calif.), in the presence or absence of phosphatidylserine (5 mg/ml, Avanti Polar Lipids, Alabaster, Ala.), and PKC iota/lambda (184 ng, 0.2 pmol/min per assay) or PKM zeta (4 ng, 0.2 pmolmin-1/assay), in the presence or absence of NSA at concentrations given on the X axis. The reaction, initiated with the addition of 50 mM ATP (final concentration, ~1-3 μCi [γ-32P]/assay), was for 30 min at 30° C., which is in the linear range for enzyme concentration (data not shown). The reaction was stopped by addition of 25 ml of 100 mM cold ATP and 100 mM EDTA, and 40 ml of the reaction mixture was spotted onto phosphocellulose paper and counted by liquid scintillation. Activity was measured as the difference between counts incorporated in the presence and absence of enzyme. Autonomous kinase activity is defined as activity in the absence of phosphatidylserine. FIG. 2 shows results with PKC zeta; similar inhibition was obtained with PKM zeta. Thus, as disclosed herein, administering NSA inhibits activity of PKC zeta and PKM zeta.

Figure 3:
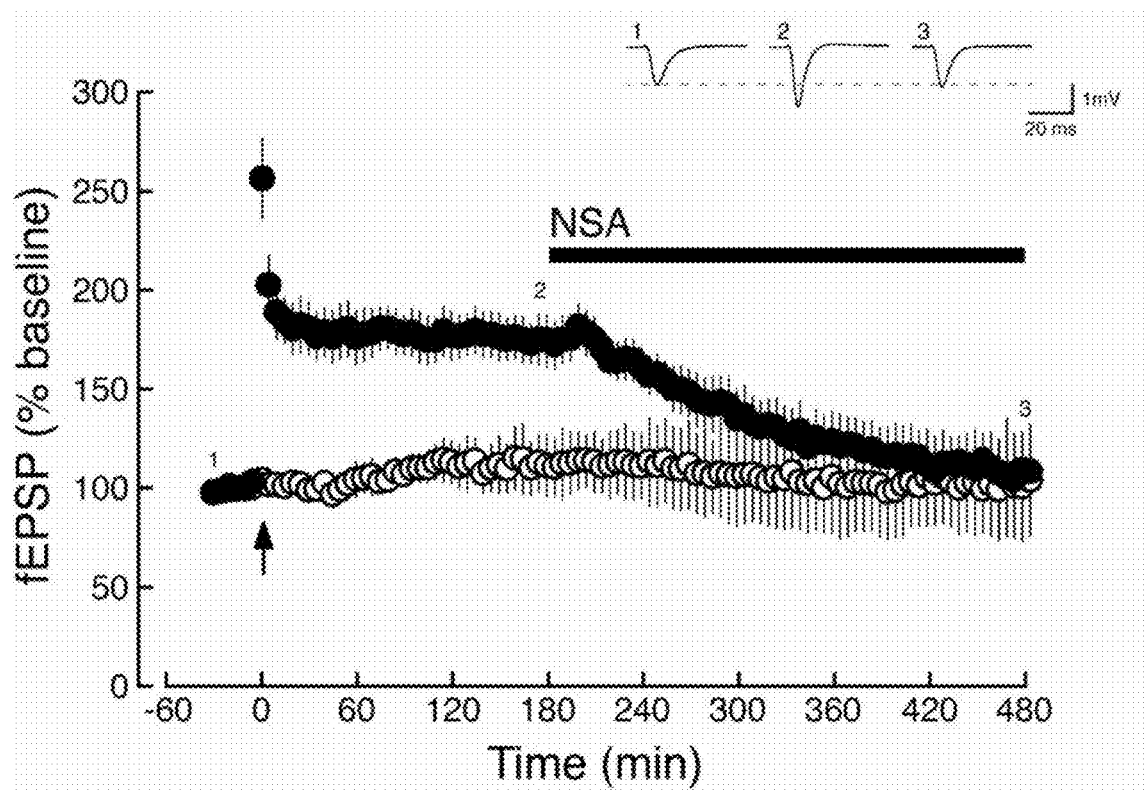
FIG. 3 is a graph showing NSA's ability to reverse maintenance of long-term potentiation (LTP) when applied three hours after application of tetanizing hippocampal stimulation in wild-type mice.
Figure 4:
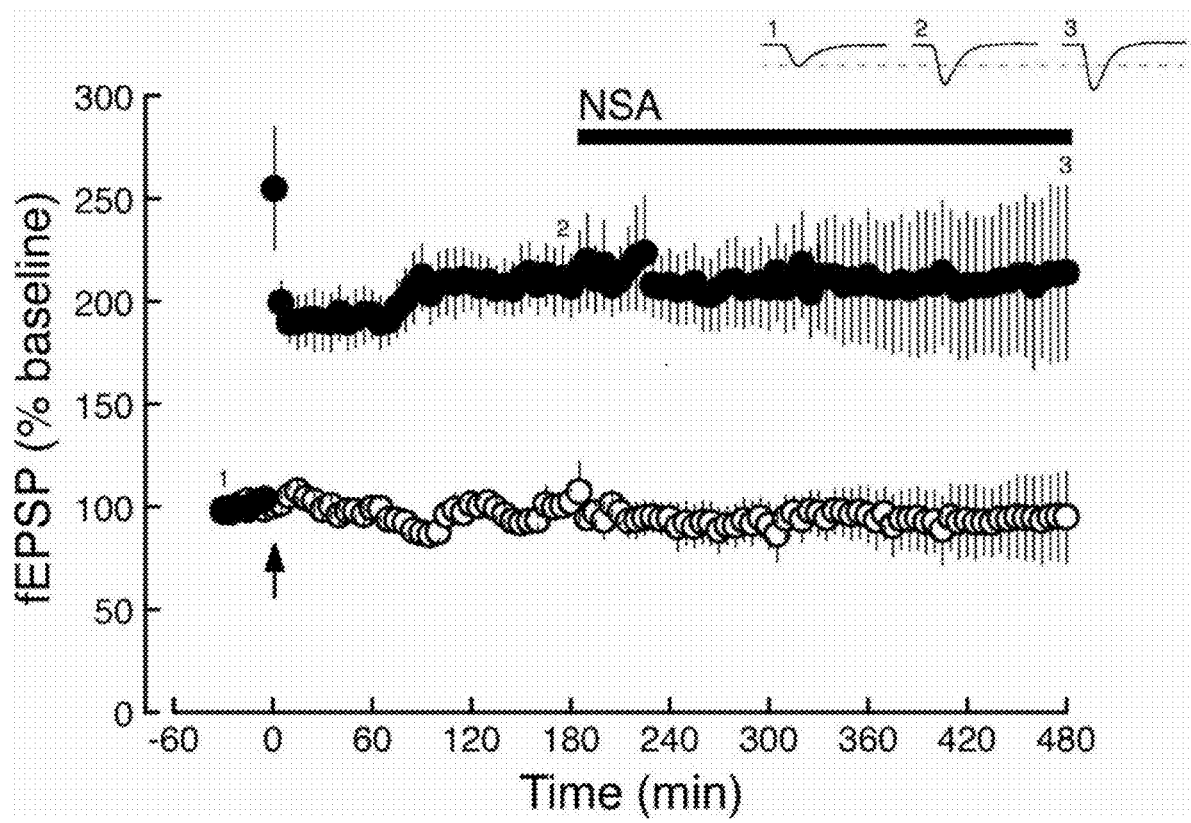
FIG. 4 is a graph demonstrating the NSA does not affect LTP maintenance in PKCzeta/PKMzeta null mice.

As shown in FIG. 3, NSA (10 μM) reverses maintenance of LTP induced by tetanizing stimulation in hippocampal slices from wild-type mice when applied 3 h post-tetanization. Acute mouse hippocampal slices (450 μm) were dissected, bathed in ice-cold dissection buffer, and sliced with a McIlwain tissue slicer in a cold room (4° C.). The dissection buffer contained (in mM): 125 NaCl, 2.5 KCl, 1.25 $NaH_2PO_4$, 26 $NaHCO_3$, 11 glucose, 10 $MgCl_2$, and 0.5 $CaCl_2$, and was bubbled with 95% $O_2$/5% $CO_2$ to maintain the pH at 7.4. The slices were immediately transferred into an interface recording chamber (31.5±1° C.). The recording superfusate consisted of (in mM): 118 NaCl, 3.5 KCl, 2.5 $CaCl_2$, 1.3 $MgSO_4$, 1.25 $NaH_2PO_4$, 24 $NaHCO_3$, and 15 glucose, bubbled with 95% $O_2$/5% $CO_2$, with a flow rate of 0.5 ml/min. Field EPSPs were recorded with a glass extracellular recording electrode (2-5 MW) placed in the CA1 stratum radiatum, and concentric bipolar stimulating electrodes were placed on either side within CA3 or CA1 Hippocampal slices were excluded from study if initial analysis showed fEPSP spike threshold was <2 mV. Pathway independence was confirmed by the absence of paired-pulse facilitation between the two pathways. The high-frequency stimulation consisted of standard two 100 Hz-1 s tetanic trains, at 25% of spike threshold, spaced 20 s apart, which is optimized to produce a relatively rapid onset of protein synthesis-dependent late-LTP. The maximum slope of the rise of the fEPSP is analyzed on a PC using the WinLTP data acquisition program. Application of NSA (black bar) beginning 3 hr after application of high-frequency stimulation reversed the maintenance of LTP seen during this time period, which is known to require PKC zeta/PKM zeta activity. In contrast, in mice genetically engineered to lack expression of PKC zeta/PKM zeta, application of NSA had no effect on maintenance of LTP, indicating recruitment of other molecular mechanisms for the maintenance of LTP in such mice (FIG. 4). Thus, administration of NSA following formation of LTP, during the maintenance phase of LTP, inhibits the maintenance of LTP, indicating that NSA inhibits mechanisms related to experience-dependent modification of synaptic plasticity and to memory formation.

In wild-type mice, maintenance of long-term memory is known to be dependent upon the function of PKC zeta/PKM zeta, but in mice unable to express PKC zeta/PKM zeta, PKC iota/lambda functionally compensates for the missing PKC zeta/PKM zeta. As disclosed herein, selectivity of NSA for the PKC zeta/PKM zeta isoform is clearly demonstrated in a hippocampal slice preparation since NSA inhibits LTP maintenance in hippocampus of wild-type but not of PKC zeta/PKM zeta null mice, which use compensatory PKC iota/lambda for LTP maintenance.

Figure 5:
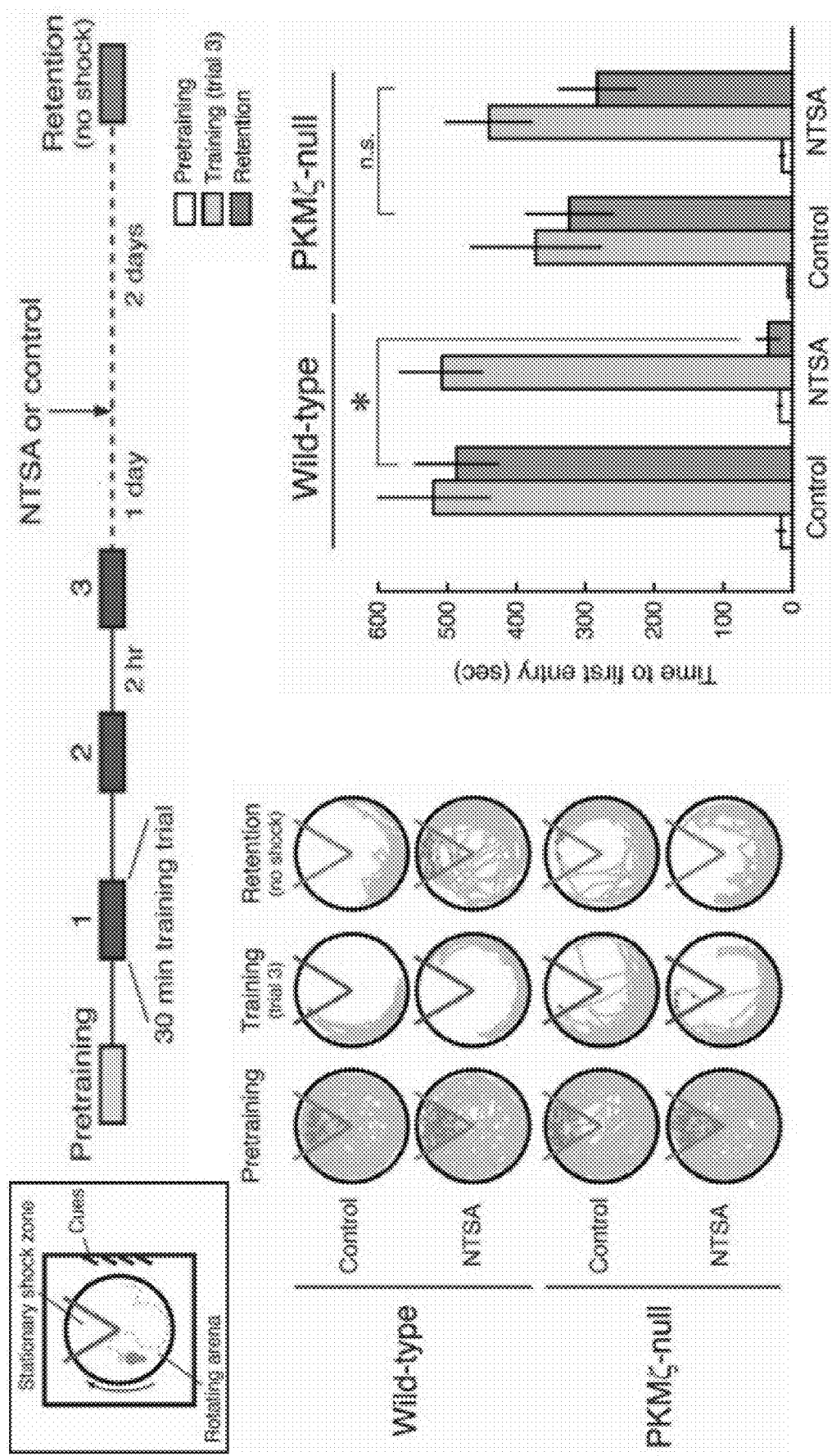
FIG. 5 shows a protocol for assessing effects of NSA (referred to as "NTSA" in FIG. 5) on long-term memory in mice and disruption of long-term memory by NSA in wild-type mice but not in PKC zeta/PKM zeta null mice.

FIG. 5 shows the behavioral effects of NSA administration in an animal model of learning and memory. A commercial computer-controlled active place avoidance system was used (Bio-Signal Group, Acton, Mass.). The position of the mouse on a 40 cm diameter circular arena rotating at 1 rpm was determined 30 times per second by video tracking from an overhead camera (Tracker, Bio-Signal Group). All experiments used the 'Room+Arena-' task variant that challenges the mouse on the rotating arena to avoid a shock zone that was a stationary 60° sector. A constant current foot-shock (60 Hz, 500 ms) was delivered after entering the shock zone for 500 ms and was repeated each 1500 ms until the mouse left the shock zone. The arena rotation periodically transported the animal into the shock zone, forcing it to actively avoid the location of shock. The shock amplitude was 0.2 or 0.3 mA, which was determined for each animal in the first session to be the minimum that elicited flinch or escape responses.

A clear wall made from Polyethylene Terephtalate Glycol-modified (PET-G) prevented the animal from jumping off the elevated arena surface. A 5-pole shock grid was placed on the rotating arena, the centroid of the mouse was tracked by the video tracker, and the shock was scrambled across the 5-poles when the mouse entered the shock zone. Every 33 ms, the software determined the mouse's position, whether it was in the shock zone, and whether to deliver shock. The time series of the tracked positions was analyzed offline (TrackAnalysis, Bio-Signal Group) to extract a number of end point measures. The time to first enter the shock zone estimates ability to avoid shock and was taken as an index of between-session memory.

A pretraining habituation period on the apparatus equivalent in time to a training session, but without shock, was provided. The training schedule was as follows. The animals received three 30 min training trials, with an intertrial interval of 2 hr. NSA was microinjected (5 nmol in 0.5 μl/hippocampus) 1 day after active place avoidance training. Retention testing was a 30 min trial without shock on the next day. The mouse trajectories depict the locations that were visited during the first 10 min, the time frame during which mice that learn the avoidance tend only rarely to enter the shock zone.

As shown in FIG. 5, in wild-type mice, administration of NSA one day after training, a time-period during which long-term memory processes related to memory maintenance are active, inhibited retention of avoidance when tested 2 days later. In mice genetically engineered to lack expression of PKC zeta/PKM zeta (PKCζ-null), in contrast, NSA administration did not affect retention testing, indicating recruitment of other molecular mechanisms for the maintenance of LTP in such mice. The bar graph shows mean±SEM. There is a significant interaction between the effects of genotype (wild-type, PKM zeta-null) and treatment (control, NSA) ($F_{1,20}=5.89$, p=0.025). The individual effects of genotype and treatment are ($F_{1,20}=0.51$, P=0.48) and ($F_{1,20}=4.29$, p=0.05), respectively. Memory retention in the wild-type mice treated with NSA differs from the wild-type control group (*, significant post-hoc test; wild-types, n's=5, PKM zeta-nulls, control, n=6, NSA, 8). Thus, application of NSA after training in an animal model of learning and memory interfered with memory indicating amnestic effects of NSA. Selectivity of NSA for the PKC zeta/PKM zeta isoform is clearly demonstrated since NSA inhibits long-term memory maintenance in wild-type but not in PKC zeta/PKM zeta null mice, which use compensatory PKC iota/lambda for long-term memory maintenance.

Figure 6:
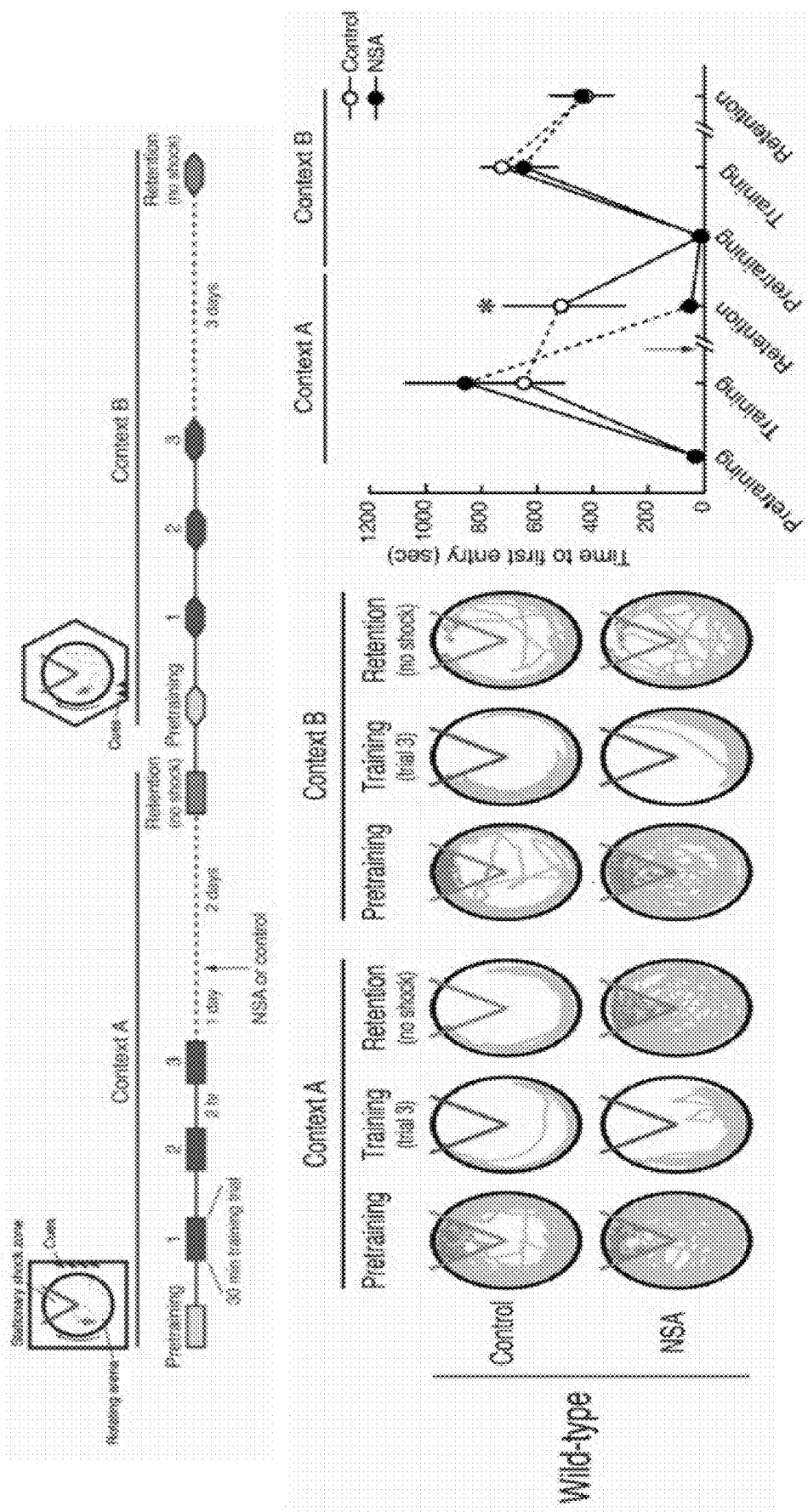
FIG. 6 shows a protocol for assessing recovery of memory after NSA's transient effects wore off and lack of permanent deleterious effects of NSA on long-term memory mechanisms.

As shown in FIG. 6, after PKC zeta/PKM zeta-selective inhibitor disruption of established long-term memory in wild-type mice by NSA, subsequent long-term memory is normal, indicating NSA may specifically disrupt long-term memory without damaging the hippocampus or causing other long-term interference with mechanisms of learning or memory beyond those affected during administration. Above, representative diagram of training protocol, similar to that described for FIG. 5. After training, memory erasure by NSA injection in hippocampus, and retention testing in one context, mice are immediately retrained and retested in a different context. NSA on relearning (1-way ANOVA with repeated measurements). There is a significant interaction between the effects of treatment (control, NSA) and trials (pretraining, training, retention in two environments) ($F_{5,40}=4.41$, P=0.0027). The main effect of treatment is $F_{1,8}=3.34$, p=0.10. NSA disrupts memory retention of the pre-injection training, and has no effect on the post-injection training (*, significant post-hoc test; n's=5). Thus, the effects NSA administration has on inhibiting memory are not due to generalized, permanent damage to neural substrates responsible for learning and memory.

As these non-limiting examples demonstrate, NSA administration may be administered to inhibit kinase activity of PKC zeta/PKM zeta, interfere with maintenance of long-term potentiation, and interfere with memory. NSA inhibits kinase activity of PKC zeta/PKM zeta, inhibits LTP indicating an inhibition of cellular molecular functions related to synaptic plasticity and learning and memory, and interferes with memory in an animal model of learning and memory. As further disclosed herein, NSA may be administered to inhibit PKC zeta/PKM zeta activity and synaptic plasticity mechanisms related to learning and memory. As further disclosed herein, NSA may be administered to subjects such as animals or humans in need of medical treatment involving interference with memory-related mechanisms, such as to disrupt memory-related mechanisms involved in mood disorders, addiction, neuropathic pain, or others.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

REFERENCES

Ji, L. L. et al. Intra-hippocampal administration of ZIP alleviates depressive and anxiety-like responses in an animal model of posttraumatic stress disorder. *Behav Brain Funct* 10, 28, doi:10.1186/1744-9081-10-28 (2014).

Zanca, R. M. et al. Environmental Enrichment Increases Glucocorticoid Receptors and Decreases GluA2 and Protein Kinase M Zeta (PKMzeta) Trafficking During Chronic Stress: A Protective Mechanism? *Frontiers in behavioral neuroscience* 9, 303, doi:10.3389/fnbeh.2015.00303 (2015).

\Cohen, H., Kozlovsky, N., Matar, M. A., Kaplan, Z. & Zohar, J. Mapping the brain pathways of traumatic memory: inactivation of protein kinase M zeta in different brain regions disrupts traumatic memory processes and attenuates traumatic stress responses in rats. *Eur Neuropsychopharmacol* 20, 253-271, doi:50924-977X(10)00002-7 [pii]10.1016/j.euroneuro.2009.12.006 (2010).

Wang, Y. X. et al. Protein kinase Mzeta is involved in the modulatory effect of fluoxetine on hippocampal neurogenesis in vitro. *Int J Neuropsychopharmacol* 17, 1429-1441, doi:10.1017/51461145714000364 (2014).

Li, Y. Q. et al. Inhibition of PKMzeta in nucleus accumbens core abolishes long-term drug reward memory. *J Neurosci* 31, 5436-5446, doi:31/14/5436 [pii]10.1523/JNEUROSCI.5884-10.2011 (2011).

Shabashov, D., Shohami, E. & Yaka, R. Inactivation of PKMzeta in the NAc Shell Abolished Cocaine-Conditioned Reward. *J Mol Neurosci* 47, 546-553, doi:10.1007/s12031-011-9671-7 (2012).

Crespo, J. A. et al. Activation of PKCzeta and PKMzeta in the nucleus accumbens core is necessary for the retrieval, consolidation and reconsolidation of drug memory. *PloS one* 7, e30502, doi:10.1371/journal.pone.0030502 (2012).

Song, M. J., Jang, J. K., Kim, W. Y., Yoon, H. S. & Kim, J. H. Inhibition of PKMzeta in the nucleus accumbens core blocks the expression of locomotor sensitization induced by amphetamine. *Behavioural brain research* 241, 139-143, doi:10.1016/j.bbr.2012.12.007 (2013).

He, Y. Y. et al. PKMzeta maintains drug reward and aversion memory in the basolateral amygdala and extinction memory in the infralimbic cortex. *Neuropsychopharmacology: official publication of the American College of Neuropsychopharmacology* 36, 1972-1981, doi: npp201163 [pii]10.1038/npp.2011.63 (2011).

Xue, Y. X. et al. A memory retrieval-extinction procedure to prevent drug craving and relapse. *Science* 336, 241-245, doi:336/6078/241 [pii]10.1126/science.1215070 (2012).

Braren, S. H., Drapala, D., Tulloch, I. K. & Serrano, P. A. Methamphetamine-induced short-term increase and long-term decrease in spatial working memory affects protein Kinase M zeta (PKMzeta), dopamine, and glutamate receptors. *Frontiers in behavioral neuroscience* 8, 438, doi:10.3389/fnbeh.2014.00438 (2014).

Monti, M. C., Gabach, L. A., Perez, M. F. & Ramirez, O. A. Impact of contextual cues in the expression of the memory associated with diazepam withdrawal: involvement of hippocampal PKMzetain vivo, and Arc expression and LTP in vitro. *Eur J Neurosci*, doi:10.1111/j.1460-9568.2012.08206.x (2012).

Santerre, J. L. et al. Ethanol dose-dependently elicits opposing regulatory effects on hippocampal AMPA receptor GluA2 subunits through a zeta inhibitory peptide-sensitive kinase in adolescent and adult Sprague-Dawley rats. *Neuroscience* 280, 50-59, doi:10.1016/j.neuroscience.2014.09.003 (2014).

Ho, S. Y., Chen, C. H., Liu, T. H., Chang, H. F. & Liou, J. C. Protein kinase mzeta is necessary for cocaine-induced synaptic potentiation in the ventral tegmental area. *Biological psychiatry* 71, 706-713, doi:10.1016/j.biopsych.2011.10.031 (2012).

Velez-Hernandez, M. E. et al. Inhibition of Protein kinase Mzeta (PKMzeta) in the mesolimbic system alters cocaine sensitization in rats. *Journal of drug and alcohol research* 2, 235669, doi:10.4303/jdar/235669 (2013).

Lee, A. M. et al. Deletion of Prkcz increases intermittent ethanol consumption in mice. *Alcohol Clin Exp Res* 38, 170-178, doi:10.1111/acer.12211 (2014).

Li, X. Y. et al. Alleviating neuropathic pain hypersensitivity by inhibiting PKMzeta in the anterior cingulate cortex. *Science* 330, 1400-1404, doi:330/6009/1400 [pii] 10.1126/science.1191792 (2010).

King, T. et al. Contribution of PKMzeta-dependent and independent amplification to components of experimental neuropathic pain. *Pain* 153, 1263-1273, doi:10.1016/j.pain.2012.03.006 (2012).

Li, W., Wang, P. & Li, H. Upregulation of glutamatergic transmission in anterior cingulate cortex in the diabetic rats with neuropathic pain. *Neuroscience letters* 568, 29-34, doi:10.1016/j.neulet.2014.03.038 (2014).

Xin, Y., Liu, X., Cao, Y., Chen, Y. & Liu, C. Up-regulation of PKMzeta expression in the anterior cingulate cortex following experimental tooth movement in rats. *Arch Oral Biol* 59, 749-755, doi:10.1016/j.archoralbio.2014.04.002 (2014).

Han, J. et al. Plasticity-Related PKMzeta Signaling in the Insular Cortex Is Involved in the Modulation of Neuropathic Pain after Nerve Injury. *Neural Plast* 2015, 601767, doi:10.1155/2015/601767 (2015).

Chen, A. et al. Involvement of protein kinase zeta in the maintenance of hippocampal long-term potentiation in rats with chronic visceral hypersensitivity. *J Neurophysiol* 113, 3047-3055, doi:10.1152/jn.00929.2014 (2015).

Melemedjian, O. K. et al. BDNF regulates atypical PKC at spinal synapses to initiate and maintain a centralized chronic pain state. *Molecular pain* 9, 12, doi:10.1186/1744-8069-9-12 (2013).

Laferriere, A. et al. PKMzeta is essential for spinal plasticity underlying the maintenance of persistent pain. *Molecular pain* 7, 99, doi:1744-8069-7-99 [pii] 10.1186/1744-8069-7-99 (2011).

Marchand, F. et al. Specific involvement of atypical PKC-zeta/PKMzeta in spinal persistent nociceptive processing following peripheral inflammation in rat. *Molecular pain* 7, 86, doi:10.1186/1744-8069-7-86 (2011).

Asiedu, M. N. et al. Spinal protein kinase M zeta underlies the maintenance mechanism of persistent nociceptive sensitization. *J Neurosci* 31, 6646-6653, doi:31/18/6646 [pii] 10.1523/JNEUROSCI.6286-10.2011 (2011).

Zhang, Y. H., Kays, J., Hodgdon, K. E., Sacktor, T. C. & Nicol, G. D. Nerve growth factor enhances the excitability of rat sensory neurons through activation of the atypical protein kinase C isoform, PKMzeta. *J Neurophysiol* 107, 315-335, doi:jn.00030.2011 [pii] 10.1152/jn.00030.2011 (2012).

Khodorova, A., Nicol, G. D. & Strichartz, G. The p75NTR signaling cascade mediates mechanical hyperalgesia induced by nerve growth factor injected into the rat hind paw. *Neuroscience* 254, 312-323, doi:10.1016/j.neuroscience.2013.09.046 (2013).

An, K. et al. Spinal protein kinase Mzeta contributes to the maintenance of peripheral inflammation-primed persistent nociceptive sensitization after plantar incision. *Eur J Pain* 19, 39-47, doi:10.1002/ejp.517 (2015).

Zhao, Q. et al. Involvement of Spinal PKMzeta Expression and Phosphorylation in Remifentanil-Induced Long-Term Hyperalgesia in Rats. *Cell Mol Neurobiol*, doi: 10.1007/s10571-016-0401-0 (2016).

Tang, Y. et al. Zeta Inhibitory Peptide as a Novel Therapy to Control Chronic Visceral Hypersensitivity in a Rat Model. *PloS one* 11, e0163324, doi:10.1371/journal.pone.0163324 (2016).

Nasir, H. et al. Consistent sex-dependent effects of PKMzeta gene ablation and pharmacological inhibition on the maintenance of referred pain. *Molecular pain* 12, doi: 10.1177/1744806916675347 (2016).

Crary, J. F., Shao, C. Y., Mirra, S. S., Hernandez, A. I. & Sacktor, T. C. Atypical protein kinase C in neurodegenerative disease I: PKMζ aggregates with limbic neurofibrillary tangles and AMPA receptors in Alzheimer disease. *Journal of neuropathology and experimental neurology* 65, 319-326 (2006).

Adzovic, L. & Domenici, L. Insulin induces phosphorylation of the AMPA receptor subunit GluR1, reversed by ZIP, and over-expression of Protein Kinase M zeta, reversed by amyloid beta. *Journal of neurochemistry* 131, 582-587, doi:10.1111/jnc.12947 (2014).

Dong, Z. et al. Long-term potentiation decay and memory loss are mediated by AMPAR endocytosis. *The Journal of clinical investigation* 125, 234-247, doi:10.1172/JCI77888 (2015).

Ma, T. et al. Suppression of eIF2alpha kinases alleviates Alzheimer's disease-related plasticity and memory deficits. *Nat Neurosci* 16, 1299-1305, doi:10.1038/nn.3486 (2013).

Hara, Y. et al. Synaptic distributions of GluA2 and PKMzeta in the monkey dentate gyrus and their relationships with aging and memory. *J Neurosci* 32, 7336-7344, doi:32/21/7336 [pii]10.1523/JNEUROSCI.0605-12.2012 (2012).

Chen, C. et al. Epigenetic modification of PKMzeta rescues aging-related cognitive impairment. *Sci Rep* 6, 22096, doi:10.1038/srep22096 (2016).

Tian, D. et al. Protein kinase M zeta regulation of Na/K ATPase: a persistent neuroprotective mechanism of ischemic preconditioning in hippocampal slice cultures. *Brain Res* 1213, 127-139, doi:S0006-8993(08)00754-3 [pii] 10.1016/j.brainres.2008.03.046 (2008).

Wang, J., Meng, F., Cottrell, J. E., Sacktor, T. C. & Kass, I. S. Metabotropic actions of the volatile anaesthetic sevoflurane increase protein kinase M synthesis and induce immediate preconditioning protection of rat hippocampal slices. *The Journal of physiology* 590, 4093-4107, doi:10.1113/jphysiol.2012.233965 (2012).

Cheng, N., Hu, X., Tian, T. & Lu, W. PKMzeta knockdown disrupts post-ischemic long-term potentiation via inhibiting postsynaptic expression of aminomethyl phosphonic acid receptors. *J Biomed Res* 29, 241-249, doi:10.7555/JBR.28.20140033 (2015).

Guenther, C. H., Windelborn, J. A., Tubon, T. C., Jr., Yin, J. C. & Mitchell, G. S. Increased atypical PKC expression and activity in the phrenic motor nucleus following cervical spinal injury. *Exp Neurol* 234, 513-520, doi:10.1016/j.expneurol.2012.01.026 (2012).

What is claimed is:

1. A method, comprising administering directly to a central nervous system of a subject a therapeutically effective amount of a compound of formula:

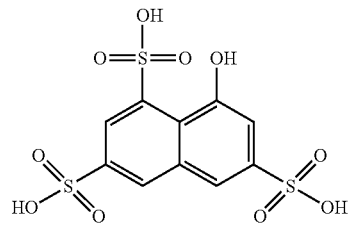 [SMILES: O=S(=O)(O)c1cc(O)c2c(S(=O)(=O)O)cc(S(=O)(=O)O)cc2c1]

or a pharmaceutically acceptable salt thereof, wherein the subject is a human in need of treatment for neuropathic pain, addiction, or anxiety.

2. The method of claim 1, wherein the administering comprises administering intracranially.

3. The method of claim 1, wherein the compound contacts neural tissue selected from cortical tissue, septohippocampal tissue, amygdalar tissue, striatal tissue, spinal cord tissue, and cerebellar tissue.

4. The method of claim 1, comprising administering the compound or pharmaceutically acceptable salt thereof admixed with a pharmaceutically acceptable excipient.

5. The method of claim 1, wherein a complex is formed between the compound and an isoform of protein kinase C zeta.

6. The method of claim 1, wherein the administering comprises administering intrathecally.

7. The method of claim 1, wherein the subject is in need of treatment for neuropathic pain.

8. The method of claim 1, wherein the subject is in need of treatment for addiction.

9. The method of claim 1, wherein the subject is need of treatment for anxiety.

* * * * *